(12) United States Patent
Van Der Zwan

(10) Patent No.: US 11,686,481 B2
(45) Date of Patent: Jun. 27, 2023

(54) PREVENTION OF MICROBIAL GROWTH IN A HUMIDIFIER THROUGH NUTRIENT LIMITATION

(71) Applicant: KONINKLIJKE PHILIPS N.V., Eindhoven (NL)

(72) Inventor: Eduard Antonius Van Der Zwan, Groningen (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 424 days.

(21) Appl. No.: 16/496,504

(22) PCT Filed: Mar. 27, 2018

(86) PCT No.: PCT/EP2018/057803
§ 371 (c)(1),
(2) Date: Sep. 23, 2019

(87) PCT Pub. No.: WO2018/178090
PCT Pub. Date: Oct. 4, 2018

(65) Prior Publication Data
US 2020/0033015 A1 Jan. 30, 2020

(30) Foreign Application Priority Data
Mar. 28, 2017 (EP) ..................................... 17163209

(51) Int. Cl.
*F24F 6/04* (2006.01)
*A61L 9/03* (2006.01)
(Continued)

(52) U.S. Cl.
CPC .............. *F24F 6/043* (2013.01); *A61L 9/037* (2013.01); *A61L 9/16* (2013.01); *F24F 2006/006* (2013.01); *F24F 2006/008* (2013.01)

(58) Field of Classification Search
CPC ........ C02F 1/447; C02F 1/04; C02F 2307/12; C02F 2101/105; C02F 1/286;
(Continued)

(56) References Cited

U.S. PATENT DOCUMENTS 4,080,290 A 3/1978 Klantschi
4,752,395 A * 6/1988 Sleytr .................. A61K 9/4825
210/490

(Continued)

FOREIGN PATENT DOCUMENTS

CN 104267080 A 1/2015
EP 0226284 6/1987
(Continued)

OTHER PUBLICATIONS

WO-2014021287-A1 Translation (Year: 2014).*
(Continued)

*Primary Examiner* — Schyler S Sanks
(74) *Attorney, Agent, or Firm* — Schott, P.C.

(57) ABSTRACT

The invention provides a humidifier apparatus (100) comprising (i) a first chamber (110) for containing water (101), (ii) a humidifying element (120) configured to facilitate evaporation and/or nebulization of water (101) contained in the first chamber (110), wherein the humidifying element (120) comprises a wick element (130), (iii) a replaceable or refillable unit (230) for containing an immobilized phosphate removing material (150), wherein the phosphate removing material (150) is configured to reduce a concentration of phosphate in water (101) before evaporation and/or nebulization of the water (101), and wherein the wick element (130) comprises the phosphate removing material (150), wherein the phosphate removing material (150) is comprised by the wick element (130) as one or more of impregnated phosphate removing material (150) and coated phosphate removing material (150), and wherein the wick element (130) is configured as the replaceable unit (230). Further, a wick element (130) comprising a phosphate removing material (150) is presented.

13 Claims, 5 Drawing Sheets

(51) Int. Cl.
*A61L 9/16* (2006.01)
*F24F 6/00* (2006.01)

(58) Field of Classification Search
CPC .......... F24F 2006/008; F24F 2006/006; F24F 6/043; A61L 9/16; A61L 9/037
See application file for complete search history.

(56) References Cited

U.S. PATENT DOCUMENTS

| | | | |
|---|---|---|---|
| 5,407,604 A | 4/1995 | Luffman | |
| 2002/0050656 A1* | 5/2002 | Ofir | F24F 6/043 261/DIG. 65 |
| 2005/0121395 A1 | 6/2005 | Landis | |
| 2008/0223789 A1* | 9/2008 | Hasan | C02F 1/54 210/684 |
| 2015/0338119 A1* | 11/2015 | MCGarva | F24F 6/043 165/229 |

FOREIGN PATENT DOCUMENTS

| | | | | |
|---|---|---|---|---|
| JP | H11257695 | | 9/1999 | |
| JP | 2007-263438 A | | 10/2007 | |
| KR | 20160061011 A | | 5/2016 | |
| WO | 2014/001952 | | 1/2014 | |
| WO | WO-2014021287 A1 | * | 2/2014 | ............ F24F 3/1603 |
| WO | WO-2014102821 A1 | * | 7/2014 | ................ F24F 6/04 |
| WO | 2015/063147 | | 5/2015 | |
| WO | WO-2016154469 A1 | * | 9/2016 | ........ B01J 20/28023 |

OTHER PUBLICATIONS

International Search Report and Written Opinion dated Jun. 25, 2018 for International Application No. PCT/EP2018/057803 Filed Mar. 27, 2018.

Time, "Hundreds of South Korean Victims of Toxic Disinfectant File Lawsuit" May 17, 2016 http://time.com/4338272/oxy-dehumidifier-disinfectant-reckitt-benckiser-korea/.

Malhotra, et al: "Nutrient Removal From Secondary Effluent By Alum Flocculation and Lime Precipitation", Int. J. Air Wat. Poll. Pergamon Press 1964. vol. 8, pp. 487-500.

"Development Report of Mineral Materials Discipline of 2016-2017", p. 58, Mar. 31, 2018.

* cited by examiner

PREVENTION OF MICROBIAL GROWTH IN A HUMIDIFIER THROUGH NUTRIENT LIMITATION

CROSS REFERENCE TO RELATED APPLICATIONS

This application is the U.S. National Phase application under 35 U.S.C. § 371 of International Application No. PCT/EP2018/057803 filed Mar. 27, 2018, published as WO 2018/178090 on Oct. 4, 2018, which claims the benefit of European Patent Application Number 17163209.4 filed Mar. 28, 2017. These applications are hereby incorporated by reference herein.

FIELD OF THE INVENTION

The invention relates to a humidifier apparatus, a kit of parts comprising such humidifier apparatus, a wick element for use in such humidifier apparatus, as well as a method of humidifying a space.

BACKGROUND OF THE INVENTION

Humidifiers are known in the art. WO2014001952, for instance, describes an evaporative humidifier comprising a water reservoir, a wick unit configured to absorb water from the water reservoir, and a fan unit arranged within a fan housing and configured to force an air flow to flow through the wick unit, wherein the fan housing comprises a top cover unit defining at least one annular air outlet at an outer part adjacent a circumference of the top cover unit.

JP11257695A discloses a humidifier with a water cleaning function. It is proposed to use an ion exchange fiber as a cleansing means to purify water in the humidifier.

WO2015063147A1 discloses a water purification method. A combination of the use of ultrafiltration and oxo-anion adsorbent prior to a reverse osmosis step is proposed to reduce biofouling.

SUMMARY OF THE INVENTION

The invention is defined by the claims.

Humidifiers are used to increase the interior humidity improving the comfort of breathing which is lacking in dry air. The devices are sold by many companies in many different markets. Generally speaking, they work according to the basic principles of nebulization or evaporation. In nebulizers, a mist of small droplets is formed by impellors or ultrasonic. If the droplets are small enough they will evaporate before landing on the ground enabling humidification. In evaporators water is directly evaporated to the air possibly helped by forcing air over the water surface or increasing the water surface by means of a wick.

It appears that in both systems microbiological growth can occur resulting in an undesirable look and smell. The aerosol droplets formed by the nebulizing humidifiers form a way of transporting the microorganism growing in humidifiers to the user possibly leading to pulmonary decease. To prevent microbial growth in the humidifier systems a biocide may be added to the water in the system, for instance via a cartridge system or by impregnation of the wick. The aerosol droplets formed by the nebulizing humidifiers form a way of transporting these biocides which may lead to risks of the user of the humidifier.

Hence, it is an aspect of the invention to provide an alternative humidifier apparatus and/or method of humidifying (a space), which preferably further at least partly obviates one or more of above-described drawbacks. The present invention may have as object to overcome or ameliorate at least one of the disadvantages of the prior art, or to provide a useful alternative.

The herein proposed invention especially prevents, or at least reduces, microbial growth by removing an essential nutrient from the water, instead of adding a toxic substance to the water. Hence, the apparatus may be safer and/or may be used longer.

Especially, in an aspect the invention provides a humidifier apparatus ("apparatus"), especially configured for humidifying an external of the humidifier apparatus, the apparatus comprising a first chamber for containing water, and a humidifying element. The humidifying element is especially configured in the first chamber and. Further, the humidifying element is especially configured to facilitate evaporation and/or nebulization of the water contained in the first chamber. Therefore, in specific embodiments the humidifying element comprises one or more of (i) a wick element and (ii) an ultrasonic device. In specific embodiments, the humidifier apparatus further comprises a replaceable or refillable unit for containing an immobilized phosphate removing material. In further specific embodiments, the humidifier apparatus (thus) further comprises an immobilized phosphate removing material. The phosphate removing material is configured to reduce a concentration of phosphate in water before evaporation and/or nebulization of the water.

In yet a further aspect, the invention also provides a method of humidifying air (in a space), wherein the method comprises evaporating and/or nebulizing water with the humidifier apparatus as defined herein. The humidifier apparatus may comprise the replaceable or refillable unit containing an immobilized phosphate removing material. Therefore, in embodiments the humidifier apparatus contains the immobilized phosphate removing material. As indicated above, the phosphate removing material is configured to reduce a concentration of phosphate in water before evaporation and/or nebulization of the water. As the phosphate removing material is configured such, that during use, or at least part of the operation time of the apparatus, this material is in contact with the (liquid) water, the phosphate concentration may (thus) be reduced before evaporation and/or nebulization of the water. The term "water" especially refers to liquid water.

With such apparatus and method, in a relatively safe way bacterial growth (within the apparatus, especially those parts in contact with water) can be prevented or inhibited. Further, with such apparatus and method it is not necessary to use biocides (though such use is not necessarily excluded). Hence, with such apparatus and method, unpleasant smells may be reduced or prevented and exposure to bacteria or biocides may also be reduced or prevented.

The apparatus comprises a first chamber for containing water. For instance, the apparatus may comprise a single chamber which can be used as reservoir (for water). The apparatus may also comprise a plurality of chambers, wherein e.g. a chamber is used as reservoir and another chamber is used as evaporation and/or nebulization chamber. The first chamber may especially be used as evaporation and/or nebulization chamber. Hence, the first chamber has one or more openings in fluid communication with the external of the apparatus. The chamber(s) may in principle have any shape.

The apparatus further comprises a humidifying element configured to facilitate evaporation and/or nebulization of the water contained in the first chamber. The element is especially configured in the first chamber. In embodiments, the humidifying element may include a wick element, an ultrasonic device, a heater, a hot rotating plate, etc. etc. Especially, however, the humidifying element comprises one or more of a wick element and an ultrasonic device. Good results can be obtained with a humidifier based on a wick element and/or based on an ultrasonic device. The former may primarily be based on evaporation; the latter may primarily be based on nebulization. Both embodiments of the apparatus are herein indicated as humidifier apparatus. The term "humidifying element" may refer to one or more (different types of) humidifying elements.

Humidifiers that are based on wick elements are known in the art, and are e.g. described in the above mentioned WO2014001952, which is herein incorporated by reference. Examples of a wick element are a water screen, a water absorbing medium or a filter that absorbs water from the chamber. For instance, the wick element may be a paper, or other water absorbing material, strip which sucks water. In this way, water rises in the wick above the water level and may then evaporate. Optionally, evaporation may be enhanced by a blower (see also below).

In embodiments, the wick element may be configured stationary, for instance in contact with a bottom of the first chamber. In specific embodiments, the wick element may be configured rotatable (especially in a vertical plane during use), and the apparatus may further comprise an actuator, such as especially an electromotor, configured to rotate the wick element. During rotation, at least part of the wick element may in the water in the first chamber, and part may be above the water level. In this way, water may evaporate. Optionally, evaporation may be enhanced by a blower (see also below).

Humidifiers that are based on nebulizers are also known in the art, and are e.g. described in U.S. Pat. No. 5,407,604, which is herein incorporated by reference.

Hence, in embodiments the humidifier apparatus further comprises an air blower configured for further facilitating evaporation and/or nebulization of water. Especially, such air blower may facilitate evaporation. The air blower may e.g. be a fan, etc. The air blower, such as a fan, creates an air flow which may pass through (and/or along) the wick and carries moisture into the room, thus aiding in the evaporation of the water within the wick and the enhancement of humidity.

In embodiments, the humidifier apparatus further comprises an immobilized phosphate removing material). Hence, this phosphate removing material is not a metal or salt that is solved in the water, but is a material that is essentially immobile. For instance, it may be comprised by the wick element, it may be provided as coating to the wick element and/or a wall of the chamber(s) or it may be available as particulate material. When particulate material is applied, at least 50 wt. % of the particles have particle sizes of especially at least 10 µm, such as especially at least 100 µm. Hence, a $d_{3,2}$ value of the particles may be at least 50 µm, such as at least 0.1 mm, like at least 0.3 mm, such as in the range of 0.5-10 mm.

In specific embodiments, the particle size of the particulate material, as measured using standard sieves may be at least 100 µm, or at least 200 µm, or up to 500 µm, such as from 300-420 µm. Particles in the range of 300-420 µm may be obtained, for example, using a 0.420 mm sieve (ASTM mesh No. 40) to remove the larger particles and then a 0.297 mm sieve (ASTM mesh No. 50) to filter out the smaller fragments and retain those in the desired size range. A narrower range could be obtained using a combination of 0.354 mm and 0.297 mm sieves or a combination of 0.297 mm and 0.250 mm sieves, for example.

With particles, the risk on evaporation (of such particles) is essentially zero, and with these particle sizes the risk on nebulization is also relatively low or essentially zero. Hence, in embodiments the phosphate removing material is comprised by a particulate material. If desired, the particles may also be contained in a container (see further also below), to further minimize any risk. Therefore, in specific embodiments the phosphate removing material is contained (as particulate material) by the humidifier apparatus.

The phosphate removing material is configured to reduce a concentration of phosphate in water before evaporation and/or nebulization of the water. By reducing the phosphate concentration, the risk on bacterial growth is reduced and bacterial growth per se is reduced or even inhibited. Hence, in this way the source of possible problems is addressed. In a specific embodiment, the phosphate removing material comprises ferritin. An example of (hyper thermophilic) ferritin is described in US20080223789, which is herein incorporated by reference. Enzymes having an analogous functionality, i.e. the ability to scavenge phosphate, may also be applied. Further, alternatively or additionally, the phosphate removing material may comprise one or more of an ion exchange resin or may be comprised by such resin. Further, alternatively or additionally, the phosphate removing material may comprise a material like one or more of kaolinite, montmorillonite, smectite and illite, etc., or may be comprised by such material. For instance, particulate montmorillonite may be applied. In another example, kaolinitic or smectic clay may be applied. For instance, particulate material may comprise one or more of kaolinite, montmorillonite, smectite and illite, and optionally additionally also ferritin.

In specific embodiments, the humidifier apparatus comprises a flow-through unit for transport of water within the humidifier apparatus, wherein the flow-through unit is configured for containing the phosphate removing material. Therefore, especially the humidifier apparatus comprises a flow-through unit for transport of water within the humidifier apparatus, wherein the flow-through unit comprises the phosphate removing material. The flow-through unit is thus configured to allow transport of water, through the unit. The unit may e.g. be a conduit between the two chambers. Optionally, the flow-through unit may be replaceable (see further below). The phosphate removing material may be comprised by the flow-through unit. For instance, the flow-through unit may be a filter unit comprising the phosphate removing material. For instance, the flow-through unit may be a bed or conduit comprising particles with the phosphate removing material, which unit allows transport of water through it, but phosphate will be caught by the phosphate removing material. Therefore, in specific embodiments humidifier may comprise at least two chambers for containing water, wherein the chambers are in fluid communication with each other via an opening, wherein the phosphate removing material is arranged in the opening, wherein the first chamber comprises the humidifying element, and wherein the first chamber is configured upstream of the second chamber.

Therefore, in specific embodiments the humidifier apparatus comprises at least two chambers for containing water, wherein the chambers are in fluid communication with each other via an opening, wherein the first chamber comprises the humidifying element, wherein the first chamber is configured upstream of the second chamber, and wherein the humidifier apparatus further comprises a receiver for hosting the replaceable or refillable unit, wherein in a state wherein the replaceable or refillable unit is hosted by the receiver at least part of the replaceable or refillable unit is configured in the opening.

In addition to such flow-through unit, or alternative thereto, a unit may be placed in the first chamber (or another chamber wherein water is contained). Water will get into contact with the unit and thereby the concentration of phosphate will be reduced. Therefore, in specific embodiments, the humidifier apparatus comprises a unit configured to be in contact with the water during use of the humidifier apparatus, wherein the unit is configured for containing the phosphate removing material. Hence, in embodiments the humidifier apparatus comprises a unit configured to be in contact with the water during use of the humidifier apparatus, wherein the unit comprises the phosphate removing material. The unit may be replaceable or refillable (or may be both replaceable and refillable). Especially, the replaceable or refillable unit is configured to be in contact with the water during use of the humidifier apparatus, and the replaceable or refillable unit contains the phosphate removing material.

The term "unit" may also refer to a plurality of units. For instance, when two chambers are available, both chambers may comprise a replaceable unit comprising particulate material comprising the phosphate removing material.

The units, such as described above may in embodiments be replaceable. Alternative thereto, or additionally in embodiments the units may be refillable. Therefore, in specific embodiments the humidifier apparatus comprises a replaceable or refillable unit comprising the phosphate removing material. For instance, a replaceable or refillable cartridge may be applied.

Optionally, the apparatus further comprises a stirring element or a flow generating element, configured to generate movement in the water, such that contact of water with the unit(s) may be promoted.

As indicated above, the phosphate removing material may not only be available as particulate material in the first chamber, or in an optional other chamber, or in an opening, or in a unit, such as a cartridge, etc., the phosphate removing material may also be comprised by the wick element. Hence, in specific embodiments the wick element comprises the phosphate removing material, wherein the phosphate removing material is comprised by the wick element as one or more of impregnated phosphate removing material and coated phosphate removing material. Therefore, in specific embodiments the phosphate removing material is comprised by the wick element of the humidifier apparatus. For instance, the ferrite may be immobilized to the wick element. Alternatively or additionally, cations (such as metal ions and/or polyatomic positively charged ions, such as ammonium) may be comprised by the wick element, such as available on the surface, and preferentially bind to phosphate.

As indicated above, the apparatus may comprise a replaceable or refillable unit. Thus, in specific embodiments the wick element may be configured as replaceable unit. Hence, the wick element may be replaceably configured in the apparatus.

The apparatus may further comprise a control system, e.g. in combination with a humidity sensor, configured to control the humidification by the apparatus in response to a humidity sensor. The control system may also be configured to control the humidification of the apparatus in response to a water level sensor in the chamber(s), especially the first chamber. The apparatus may be switched off, or enter a sleeping stage, when the water level is too low (including absence of water).

Alternatively or additionally, the humidifier apparatus may further comprising (i) a control system, (ii) a first sensor configured to sense a phosphate concentration in the water, and (iii) an indication system, wherein the control system may (also) be configured to indicate with the indication system upon a first sensor signal of the first sensor a phosphate concentration related signal. Therefore, in embodiments the invention also provides a method, further comprising providing with an indication system a phosphate concentration related signal in dependence of a first sensor signal of a first sensor. In this way, also the capacity of the phosphate removing material may be controlled and when necessary, the user may replace the phosphate removing material, such as by replacing a cartridge.

Alternatively or additionally, the humidifier apparatus may further comprise (i) a control system, (ii) a second sensor configured to sense one or more of (iia) a phosphate removing material amount, and (iib) a replacement or refill of the replaceable or refillable unit, and (iii) an indication system, wherein the control system is configured to indicate with the indication system upon a second sensor signal of the second sensor a replace or refill signal. Therefore, in embodiments the invention also provides a method, further providing with an indication system a replace or refill signal in dependence of a second sensor signal of a second sensor, wherein the second sensor is configured to sense one or more of (iia) a phosphate removing material amount, and (iib) a replacement or refill of the replaceable or refillable unit.

The indication system may be configured to display a message (e.g. "replace phosphate removing material" or "replace cartridge", "refill cartridge", etc. etc.), to produce a sound signal, to produce a light signal, etc. etc. The indication system will display such message and/or provide such sound and/or light signal upon instruction of the control system.

The apparatus may be provided with or without unit comprising phosphate removing material. For instance, the apparatus may be provided without such unit and the units may be separately sold.

Hence, the invention also relates to such apparatus with a unit receiver, configured to receive a unit comprising the phosphate removing material.

Therefore, in embodiments the invention also provides an apparatus comprising a first chamber for containing water, and a humidifying element configured to facilitate evaporation and/or nebulization of the water contained in the first chamber, wherein the humidifying element comprises one or more of a wick element and an ultrasonic device, wherein the humidifier apparatus further comprises a unit that can be (re)filled or a receiver configured to host a replaceable unit. Especially, the unit that can be (re)filled will be filled with phosphate removing material, for execution of the herein described method. Likewise, especially the receiver that can host the replaceable unit will host such replaceable unit filled with phosphate removing material, for execution of the herein described method.

Therefore, in yet a further aspect the invention also provides a kit of parts comprising one or more units, such as one or more replaceable and/or refillable units, such as at least one replaceable units, like especially a plurality of replaceable units, each comprising immobilized phosphate removing material, wherein the phosphate removing material is configured to reduce a concentration of phosphate in water, and a humidifier apparatus as defined herein configured to host such replaceable unit. As indicated above, the phosphate removing material especially comprises ferritin. Therefore, the kit of parts may also comprise one or more wick elements (comprising the phosphate removing material). Additionally or alternatively, the kit of parts may also comprise one or more cartridges (containing the phosphate removing material).

In yet a further aspect, the invention also provides the replaceable or refillable unit per se, such as a cartridge or the wick element. Therefore, in an embodiment the invention also provides a cartridge containing phosphate removing material, such as a cartridge comprising particulate material (which comprises the phosphate removing material). The cartridge may especially have openings for access of water. Yet, in further embodiments, the invention also provides a wick element comprising the phosphate removing material. For instance, the wick element may in embodiments comprise a cellulosic material, such as paper (like a laminate of (pressed) layers of paper), or cardboard. Other options, however, may also be possible. In embodiments, ferritin may be immobilized in and/or on the wick element. In yet other embodiments, particulate material may be comprised by the wick element. For instance, for making the wick element a pulp mixture may be applied comprising the phosphate removing material. Hence, the phosphate removing material may be embedded in the wick element and/or may be comprised by a surface of the wick element. Further, the phosphate removing material may be applied as coating on the wick element. Yet further, the wick element may be impregnated with the phosphate removing material. Therefore, in embodiments the wick element is configured as replaceable wick element, allowing replacement of the wick element. The wick element is especially an element that has capillary forces/provides capillary effects. In this way, water may be sucked in the material and may rise along at least part of the height of the wick element (when the wick element is in contact with water and is e.g. configured vertical). Wick elements per se are known in the art.

Hence, the invention provides amongst others the use of ferritin (or other suitable materials as indicated above) as a phosphate removing material in a humidifier apparatus (for removing phosphate from water in such apparatus).

The term "an external of the humidifier apparatus" especially refers to the atmosphere which contains the humidifier apparatus. Especially, the apparatus may be used indoor. Hence, an external of the apparatus may refer to a space which contains the apparatus. The term "space" may for instance relate to a (part of) hospitality area, such as a restaurant, a hotel, a clinic, or a hospital, etc. The term "space" may also relate to (a part of) an office, a department store, a warehouse, a cinema, a church, a theatre, a library, etc. However, the term "space" also relate to (a part of) a working space in a vehicle, such as a cabin of a truck, a cabin of an air plane, a cabin of a vessel (ship), a cabin of a car, a cabin of a crane, a cabin of an engineering vehicle like a tractor, etc. The term "space" may also relate to (a part of) a working space, such as an office, a (production) plant, a power plant (like a nuclear power plant, a gas power plant, a coal power plant, etc.), etc. For instance, the term "space" may also relate to a control room, a security room, etc.

The apparatus may also be comprised by a system, which system may include also one or more other apparatus such as an air conditioning system, a heating system, a ventilation system, etc. Further, the apparatus may also be comprised by a system comprising a plurality of such humidifier apparatus. Such system may include a control system for controlling the one or more apparatus comprised by the system.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF THE EMBODIMENTS

Figure 1A:
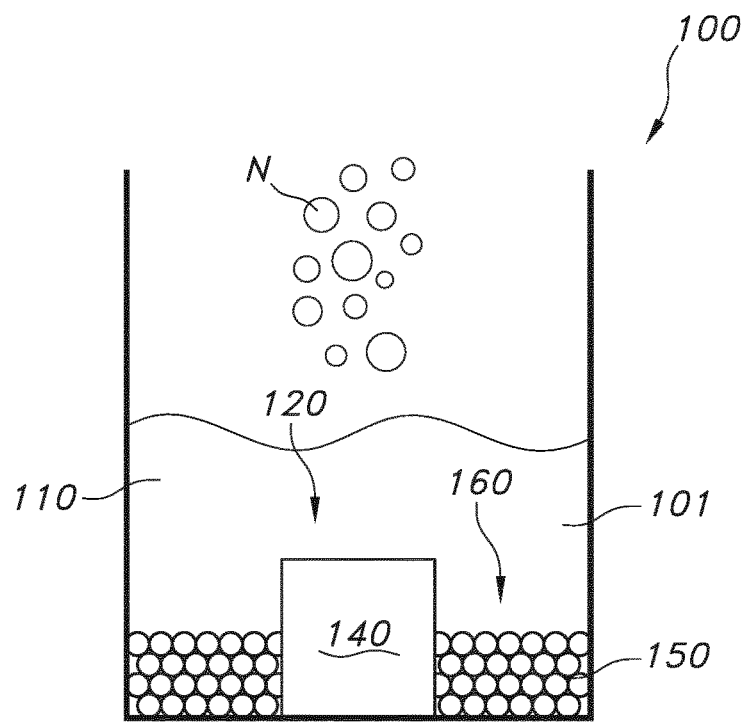
FIGS. 1a-1g schematically depict some embodiments of the humidifier apparatus.
Figure 1B:
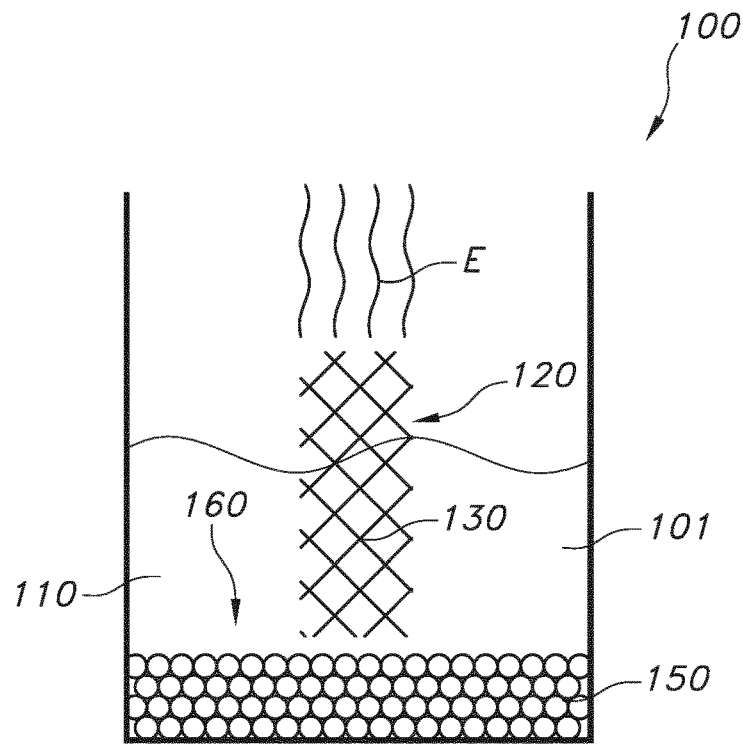
Figure 1C:
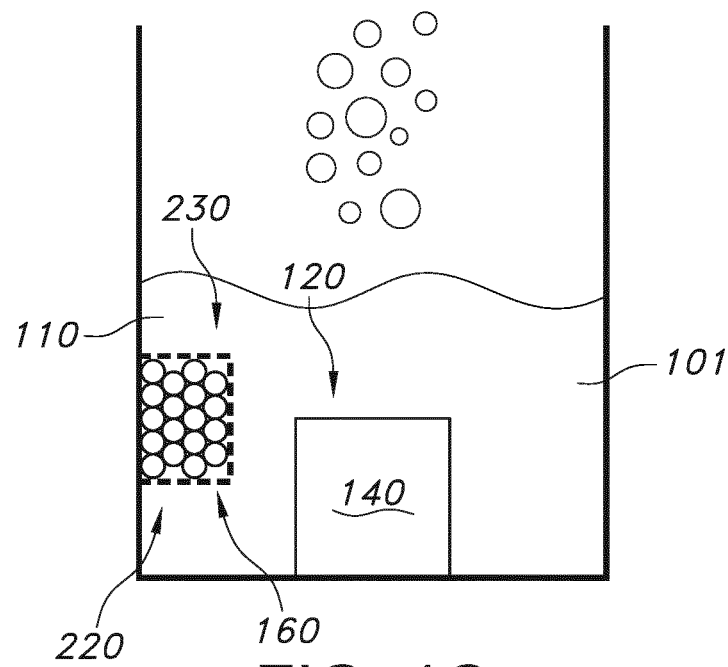
Figure 1D:
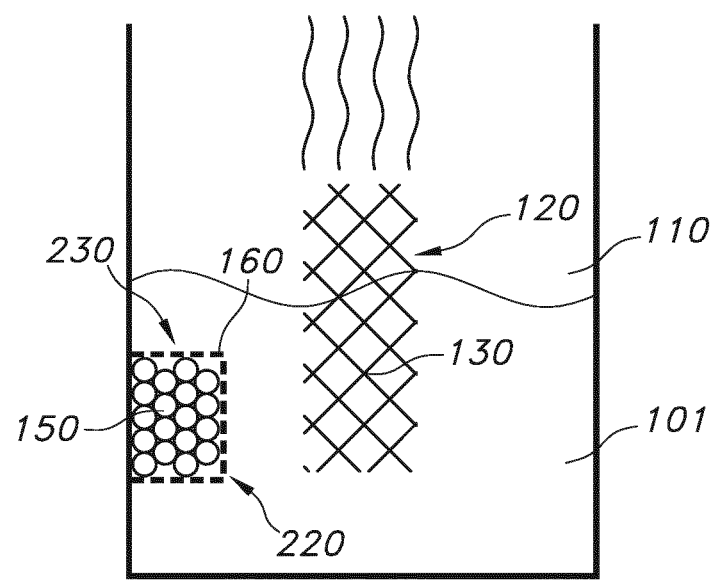
Figure 1E:
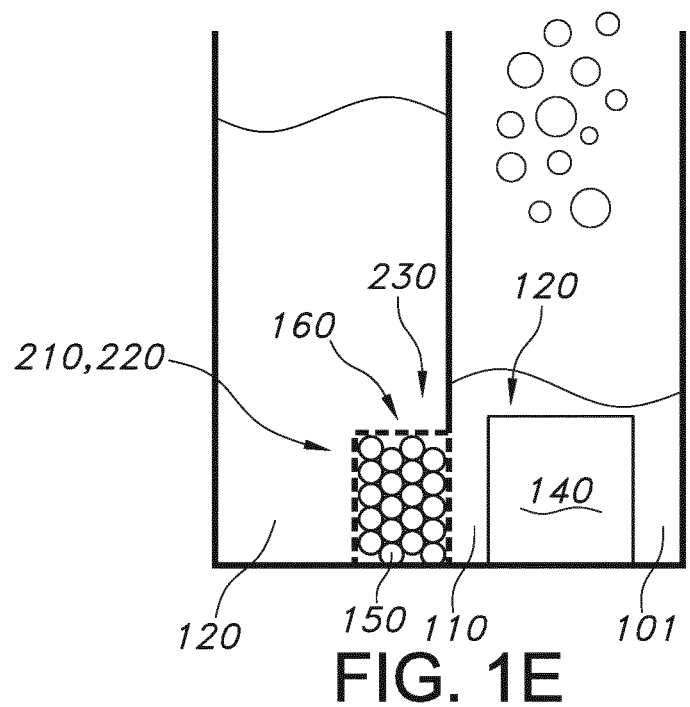
Figure 1F:
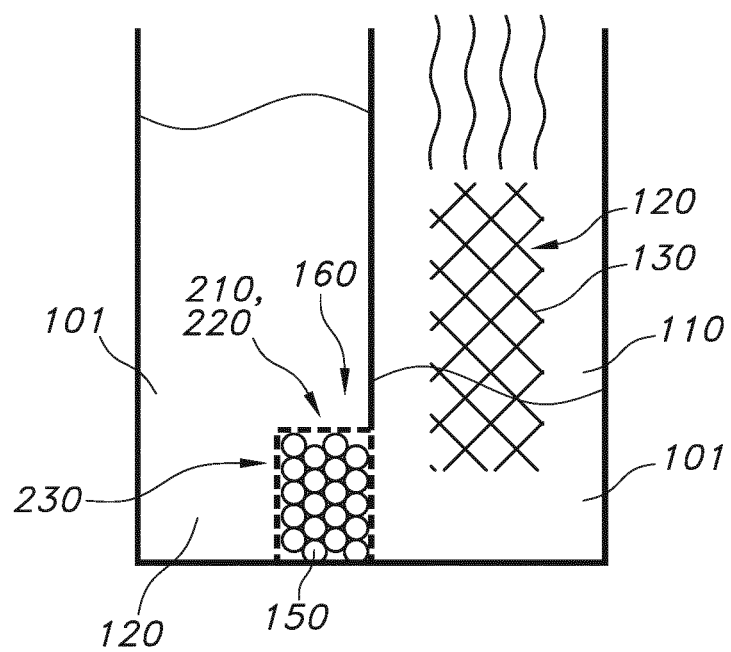
Figure 1G:
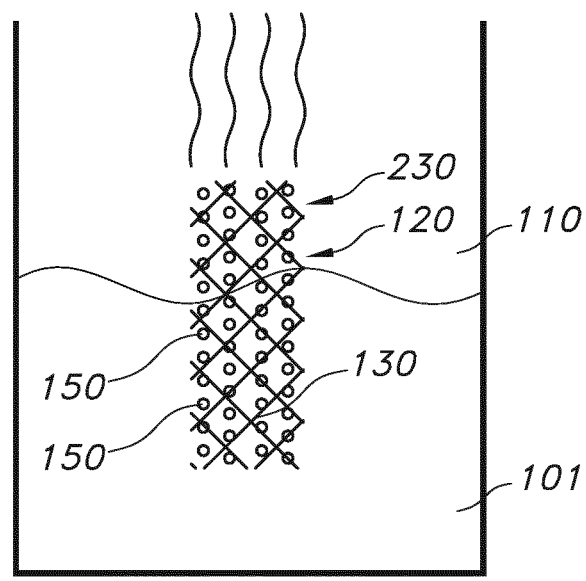

FIGS. 1a-1b schematically depicts embodiments with particulate material (which comprises phosphate removing material) on the bottom of the apparatus. FIGS. 1c-1d schematically depict embodiments with particulate material in a unit, such as a replaceable unit. FIGS. 1e and 1f schematically depicted embodiments with particulate material in a unit or bed in between two compartments, such as a flow-through unit. FIG. 1g schematically depicts an embodiment wherein the wick element is coated or impregnated with the phosphate removing material. FIGS. 1a, 1c, and 1e schematically depict embodiments with an ultrasonic device; and FIGS. 1b, 1d, 1f and 1g schematically depict embodiments with a wick element. Combinations of wick elements and ultrasonic devices may also be applied.

In FIGS. 1a-1g schematically embodiments of humidifier apparatus 100 are shown. The apparatus comprises (i) a first chamber 110 for containing water 101 and (ii) a humidifying element 120 configured to facilitate evaporation and/or nebulization of water 101 contained in the first chamber 110. The humidifying element 120 comprises one or more of a wick element 130 and an ultrasonic device 140. The apparatus 100 may further comprise (iii) a replaceable or refillable unit 230 for containing an immobilized phosphate removing material 150, wherein the phosphate removing material 150 is configured to reduce a concentration of phosphate in water 101 before evaporation and/or nebulization of the water 101. Reference N indicates nebulized droplets. Reference E indicates evaporated water.

In specific embodiments, the apparatus 100 comprising a unit 220, such as a replaceable or refillable unit 230, configured to be in contact with the water 101 during use of the humidifier apparatus 100 (see e.g. FIGS. 1a-1f, and also FIG. 1g, as in embodiments also the wick element 130 may be is configured as replaceable unit). The unit 220 is configured for containing the phosphate removing material 150. For instance, the humidifier apparatus may comprise a flow-through unit 210 for transport of water 101 within the humidifier apparatus 100. The flow-through unit 210 is configured for containing the phosphate removing material 150 (see e.g. FIGS. 1e and 1f). Reference 160 indicates particulate material, which may comprise the phosphate removing material 150. Thereby, this material is immobilized.

Figure 2A:
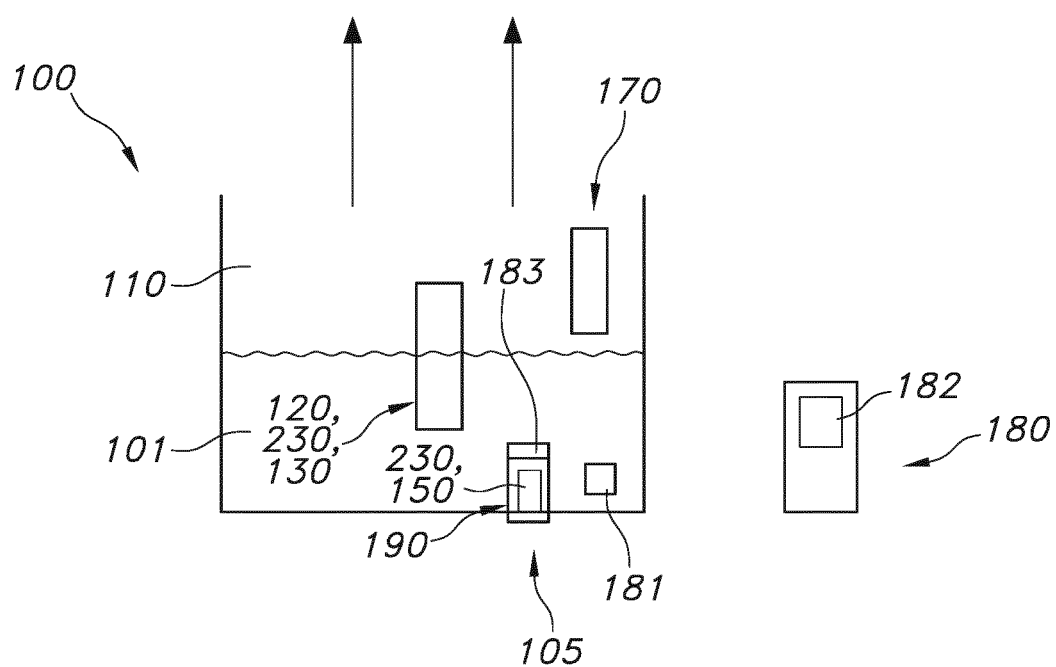
FIGS. 2a-2b schematically depicts some further aspects of the invention The schematic drawings are not necessarily to scale.

FIG. 2a schematically depicts some embodiments and variants in a single figure. Hence, in a single apparatus 100 not all elements schematically depicted in FIG. 2a are necessarily present.

The humidifier apparatus 100 in FIG. 2a further comprises an air blower 170 configured for further facilitating evaporation and/or nebulization of water 101. Further, humidifier apparatus 100 in FIG. 2a shows an embodiments wherein the apparatus 100 further comprising a control system 180, a first sensor 181 configured to sense a phosphate concentration in the water 101, and an indication system 182. The control system 180 may e.g. be configured to indicate with the indication system 182 upon a first sensor signal of the first sensor 181 a phosphate concentration related signal. For instance, the first sensor 181 may comprise one or more of a potentiometric ion-selective electrode, an amperometric electrode and a potentiometric enzyme electrode, etc.

The humidifier apparatus 100 in FIG. 2a further comprises by way of example a second sensor 183 configured to sense one or more of (a) a phosphate removing material amount, and (b) a replacement or refill of the replaceable or refillable unit 230 (for instance on the basis of an interruption of a contact or on the basis of making electrical contact, etc.). The control system 180 may especially be configured to indicate with the indication system 182 upon a second sensor signal of the second sensor 183 a replace or refill signal. Such sensor may be a presence sensor, a movement sensor, a contact sensor (sensing the opening of a shutter or the like of a cavity or receiver 190 configured to host the phosphate removing material, such as a replaceable or refillable unit 230). Hence, FIG. 2a also shows a receiver 190 configured to host a replaceable unit 230 or optionally a refillable unit 230. Hence, the refillable unit may be configured permanent or may be configured removable from the apparatus 100. Reference 105 indicates a shutter or the like for closing (water tight) the receiver 190. The receiver 190 may host a replaceable cartridge or unit 230 with the phosphate removing material 150.

Figure 2B:
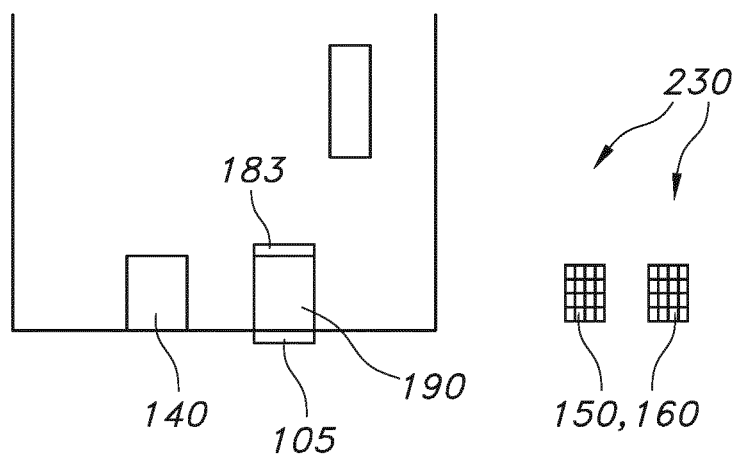

FIG. 2b schematically depicts an embodiment of a kit of parts 1000 comprising a plurality of replaceable units 230, each comprising immobilized phosphate removing material 150. As indicated above, the phosphate removing material 150 is configured to reduce a concentration of phosphate in water (available in the apparatus 100 during use of the apparatus), and (thus) a humidifier apparatus 100 configured to host such replaceable unit 230.

Hence, amongst others the invention provides a powder of the nutrient absorbing material placed on the bottom of the water container. In embodiments, a powder of the nutrient absorbing material is put in a cartridge which is placed in the water container. Yet, in further embodiments, such as in systems were water is slowly added to the humidifying area through a valve a particle bed of nutrient absorbing material is placed near this valve. This ensures the essential nutrients are absorbed from the water before it enters the humidifying area. For systems were a wick is used to increase the humidifying area the wick can be impregnated with a nutrient absorbing material. With the herein described apparatus, limitation of microbial growth in a humidifier through nutrient may be obtained.

The term "substantially" herein, such as in "substantially consists", will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of". The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices herein are amongst others described during operation. As will be clear to the person skilled in the art, the invention is not limited to methods of operation or devices in operation.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to". The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention further applies to a device comprising one or more of the characterizing features described in the description and/or shown in the attached drawings. The invention further pertains to a method or process comprising one or more of the characterizing features described in the description and/or shown in the attached drawings.

The various aspects discussed in this patent can be combined in order to provide additional advantages. Further, the person skilled in the art will understand that embodiments can be combined, and that also more than two embodiments can be combined. Furthermore, some of the features can form the basis for one or more divisional applications.

The invention claimed is:

1. A humidifier apparatus, comprising:
   a first chamber for containing water;
   a humidifying element configured to facilitate evaporation and/or nebulization of the water contained in the first chamber, wherein the humidifying element comprises a wick element; and
   a first replaceable or refillable unit provided at a wall of the first chamber for containing an immobilized phosphate removing material, wherein the phosphate removing material is configured to reduce a concentration of phosphate in the water before the evaporation and/or nebulization of the water,
   wherein the wick element comprises the phosphate removing material, wherein the wick element is impregnated with the phosphate removing material and coated with the phosphate removing material, and wherein the wick element is configured as a second replaceable or refillable unit.

2. The humidifier apparatus according to claim 1, wherein the phosphate removing material is comprised by a particulate material.

3. The humidifier apparatus according to claim 2, wherein a particle size of the particulate material is in a range of about 300 μm to 420 μm.

4. The humidifier apparatus according to claim 1, wherein the phosphate removing material comprises ferritin.

5. The humidifier apparatus according to claim 1, further comprising an air blower configured for further facilitating the evaporation and/or nebulization of the water.

6. The humidifier apparatus according to claim 1, further comprising (i) a control system, (ii) a sensor configured to sense the concentration of phosphate in the water, and (iii) an indication system, wherein the control system is configured to indicate, with the indication system upon a sensor signal of the sensor, a phosphate concentration related signal.

7. The humidifier apparatus according to claim 1, further comprising (i) a control system, (ii) a sensor configured to sense one or more of (iia) a phosphate removing material amount, and (iib) a replacement or refill of the replaceable or refillable unit, and (iii) an indication system, wherein the control system is configured to indicate, with the indication system upon a sensor signal of the sensor, a replace or refill signal.

8. The humidifier apparatus according to claim 1, further comprising an ultrasonic device.

9. The humidifier apparatus according to claim 1, wherein the phosphate removing material comprises one or more of:
ferritin;
kaolinite;
montmorillonite;
smectite; and
illite.

10. The humidifier apparatus according to claim 1, wherein the first replaceable or refillable unit is a flow through unit in fluid communication with the first chamber to allow transport of water and catch phosphate through the phosphate removing material.

11. A wick element for use in a humidifier, comprising a phosphate removing material, wherein the wick element is impregnated with the phosphate removing material and coated with the phosphate removing material, wherein the wick element is configured as a first replaceable or refillable unit for containing the phosphate removing material as an immobilized phosphate removing material, and wherein the phosphate removing material is also provided at a wall of a first chamber in a second replaceable or refillable unit in the humidifier.

12. The wick element according to claim 11, wherein the phosphate removing material is ferritin.

13. The wick element according to claim 11, wherein the phosphate removing material comprises one or more of:
ferritin;
kaolinite;
montmorillonite;
smectite; and
illite.

* * * * *